(12) United States Patent
Aflatoon

(10) Patent No.: US 9,333,093 B2
(45) Date of Patent: May 10, 2016

(54) MINIMALLY INVASIVE EXPANDABLE INTERBODY FUSION CAGE

(71) Applicant: Kamran Aflatoon, Corona del Mar, CA (US)

(72) Inventor: Kamran Aflatoon, Corona del Mar, CA (US)

(\*) Notice: Subject to any disclaimer, the term of this patent is extended or adjusted under 35 U.S.C. 154(b) by 134 days.

(21) Appl. No.: 14/180,580

(22) Filed: Feb. 14, 2014

(65) Prior Publication Data

US 2015/0230935 A1 Aug. 20, 2015

(51) Int. Cl.
*A61F 2/44* (2006.01)
*A61F 2/28* (2006.01)
*A61F 2/30* (2006.01)

(52) U.S. Cl.
CPC .......... *A61F 2/447* (2013.01); *A61F 2002/2835* (2013.01); *A61F 2002/3038* (2013.01); *A61F 2002/30462* (2013.01); *A61F 2002/30579* (2013.01); *A61F 2002/30904* (2013.01); *A61F 2002/448* (2013.01)

(58) Field of Classification Search
CPC ................ A61F 2/4455; A61F 2/4465; A61F 2002/448; A61F 2002/4485; A61F 2002/4495; A61F 2002/4415
See application file for complete search history.

(56) References Cited

U.S. PATENT DOCUMENTS

| | | | | |
|---|---|---|---|---|
| 7,252,685 | B2* | 8/2007 | Bindseil | A61F 2/4455 427/2.26 |
| 7,811,331 | B2* | 10/2010 | Johnson | A61B 17/025 606/257 |
| 2011/0082552 | A1* | 4/2011 | Wistrom | A61F 2/442 623/17.16 |

\* cited by examiner

*Primary Examiner* — Anu Ramana
(74) *Attorney, Agent, or Firm* — Ober, Kaler, Grimes & Shriver; Royal W. Craig

(57) ABSTRACT

An interbody fusion cage comprised of two support elements that separate after insertion into the interbody space to form a pocket into which graft material may be inserted. The expansion of the support elements deploys ribbons between the two support elements to further insulate the pocket into which the graft material is inserted, thereby holding it securely in place. Ribbons may be formed of a flexible material so that graft material can be inserted by a surgeon above or below them. Ribbons may also be deployed manually by the surgeon so as to allow insertion of graft material before the ribbon is deployed.

19 Claims, 5 Drawing Sheets

MINIMALLY INVASIVE EXPANDABLE INTERBODY FUSION CAGE

CROSS-REFERENCE TO RELATED APPLICATIONS

The present application claims priority from U.S. patent application Ser. No. 13/892,724 filed May 13, 2013, which is incorporated herein by reference.

BACKGROUND OF THE INVENTION

1. Field of the Invention

The present invention relates generally to devices and methods for treating spinal disorders and more specifically to an intervertebral device for aligning and maintaining the relative position of two or more adjacent vertebrae as well as to contain graft material to facilitate immobilization of the vertebra through fusion to eliminate the pain caused by abnormal motion.

2. Description of the Background

Degeneration of the intervertebral discs and the concomitant instability and translocation of the vertebra is a common cause of back pain and may result from a variety of problems including congenital deformity, age related degeneration, osteoporosis, tumor and disc herniation as a result of trauma. Disc degeneration, for whatever reason, results in compression of the spinal nerve roots resulting in pain. Palliative care is often successful in mild cases but more extreme or degenerative cases may require a surgical approach to stabilize the joint and relieve pressure.

A number of surgical approaches have been developed with varying degrees of success depending on the cause and severity of the damage. A ruptured disc impinging the nerve root may be partially excised to relieve pressure. In such a case the adjacent vertebra may be further fixated using rods, screws and plates in an attempt to stabilize the spine and delay or prevent further degeneration. Patients undergoing such excisions and fixations however, often require subsequent procedures to address recurrent pain. In many case such subsequent procedures include fusion. Spinal fusion, or spondylosyndesis, is a surgical technique used to combine two or more vertebrae utilizing supplementary bone graft tissue in conjunction with the body's natural osteoblastic processes to eliminate relative movement as a source of pain. A variety of approaches to fusion are available including posterior fusion, postero-lateral fusion and anterior or posterior interbody fusion.

In the more traditional posterior fusion approach, performed in conjunction with partial excision of the ruptured disc, growth is induced between the bony vertebral laminae to fix the position of the vertebra. In the postero-lateral fusion method bone growth is induced to join the transverse processes to prevent motion between the adjacent vertebrae. However, both posterior and postero-lateral fusion tend to cause bony overgrowth leading to nerve root compression and pain by spinal stenosis. This, coupled with other risks, limitations and disappointing fusion success rates have caused surgeons searching for alternate fusion means to develop interbody fusion techniques.

Interbody fusion techniques involve complete excision and replacement of the soft disc with autograft material harvested from the patient, prepared allograft from a donor source or, more recently, bone morphogenic protein. Most commonly performed in the lumbar region, the procedure can be accomplished from an anterior approach (Anterior Lumbar Interbody Fusion or ALIF) or a posterior approach (PLIF). In either case the procedure attempts to reconstruct the normal anatomic relationships between the bony and the neural structures and has many advantages. Specifically, weight bearing through a solid bony fusion mass between vertebral bodies relieves the mechanical pain of the traditional unstable degenerative disc and generally prevents long term disc collapse or further degenerative changes. The complete disc excision prevents recurrent herniation of the same degenerated disc.

Successful fusion results in a contiguous growth of bone to create a solid mass that will unite the vertebra. When fusion graft material is first placed it is soft and movable and lacks cohesive strength and is therefore incapable of remaining in position or carrying any load without assistance. A variety of appliances have been developed that attempt to hold the vertebrae to be joined still relative to one another under normal spinal activity and daily stress in order to allow the fusion process to occur over the 18-24 month period generally required. Such appliances, often referred to as interbody cages, provide a mechanically rigid scaffold in which the graft material may be placed.

Cage designs vary widely but generally fall into three categories. Horizontal cylinders (1) are generally made from titanium and inserted by either the posterior or anterior approach into complimentary holes bored into the intervertebral space. They can be placed by open or minimally invasive techniques. U.S. Pat. No, 5,026,373 to Ray, et al. discloses a cage of this design that includes a perforated, threaded exterior surface that cat be screwed into place between the vertebra and packed with bone material. Bone growth through the perforations and into the cancelous bone of the vertebra exposed by the insertion results in the desired fusion.

A second design is in the form of a vertical cylinder or ring (2). Often referred to as a Harms cage, vertically cylindrical cages are also usually made from titanium and can be cut to length as desired so as to span larger segments of the lumbar spine. End caps are employed to prevent subsidence into the cancelous bone although this design suffers, as a result, from a requirement that its central void be packed with graft material prior to insertion. Due to its sharp edges it is most commonly inserted by open techniques. U.S. Pat. No. 5,989,290 to Biedermann et al, et al. discloses a cage of this design.

A third design form is the open box cage (3). Constructed of carbon, titanium or bio-compatible non-metallic materials, this design can be formed for an anatomical fit or to recreate the normal lumbar lordosis. Openings in the box walls permit graft material contained therein to contact the vertebral bone. Some designs utilize a single large cage. Alternately, a pair of smaller cages is utilized which can be inserted posteriorly using minimally invasive techniques. U.S. Pat. No. 6,241,769 to Nicolson et al, et al. discloses a box form cage having a central void having an open top and bottom and a dovetail system for structurally attaching the device to the adjacent vertebra which are prepared by cutting cooperative channels into their surfaces.

Cages provide enhanced mechanical stability prior to fusion, maintain the intervertebral disc height and ultimately provide a high rate of successful fusion. The ideal cage should rigidly immobilize the spine in all directions, be strong enough to withstand repeated loadings, and have a modulus of elasticity similar to that of cortical bone. It should also be easy to insert by open or minimally invasive methods, resist subsidence, translation or retropulsion and be clinically effective. Cage designs further must balance the competing priorities of being small enough to be inserted through the incisions of minimally invasive techniques while also being large enough to fill a significant portion of the interbody space and present a significant area to the vertebral surface in which graft material can be inserted and retained to promote growth.

It would be therefore an improvement in this art to provide an interbody fusion cage for facilitating vertebral fusion and thereby eliminating spinal back pain caused by ruptured or degenerated vertebral discs which overcomes the deficiencies of prior known devices. Thus, it is an object of the present invention to provide an interbody fusion cage of open form design that can easily be placed in the evacuated interbody space to constrain relative vertebral motion and which can subsequently be secured again translation and retropulsion. It is a further object of the present invention to provide an interbody fusion cage that is sufficiently robust so as to withstand the forces imposed by normal daily activity on the part of the patient and which is clinically effective it retaining osteoconductive or osteoinductive material so as to facilitate fusion. It is a further object of the present invention to provide an interbody fusion cage that allows the surgeon easy access to the point of insertion of the graft material while providing maximum protection against graft material movement out of the interbody space.

SUMMARY OF THE INVENTION

Accordingly, there is provided an interbody fusion cage for insertion into the interbody space between adjacent vertebrae to promote fusion. The interbody fusion cage is comprised of two support elements that separate after insertion into the interbody space to form a pocket into which graft material may be inserted. The expansion of the support elements causes one or more ribbons to extend between the two support elements to further enclose the pocket into which the graft material is inserted, thereby holding it securely in place. In an alternate embodiment, a suture or similar filament is used to pull the ribbon(s) across the opening between the two structural elements after insertion of the graft material so as to provide the surgeon with easy access to the pocket formed between the elements. In yet another embodiment a combination of ribbon and suture mechanisms are utilized so as to achieve maximum protection from graft material movement while allowing the surgeon maximum access to the pocket into which to insert the material.

The foregoing objects, features and attendant benefits of this invention will, in part, be pointed out with particularity and will become more readily appreciated as the same become better understood by reference to the following detailed description of a (preferred embodiment and certain modifications thereof when taken in conjunction with the accompanying drawings.

DETAILED DESCRIPTION OF THE PREFERRED EMBODIMENTS

Figure 1:
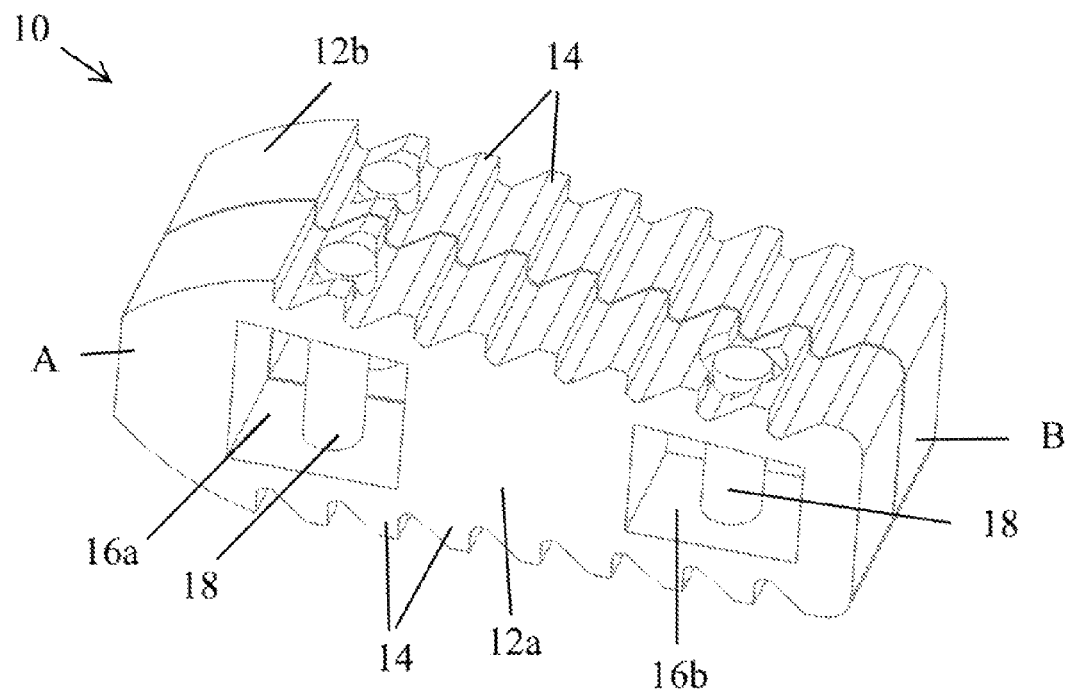
FIG. 1 is a three-quarters perspective view of an embodiment according to the present invention from the side.
Figure 2:
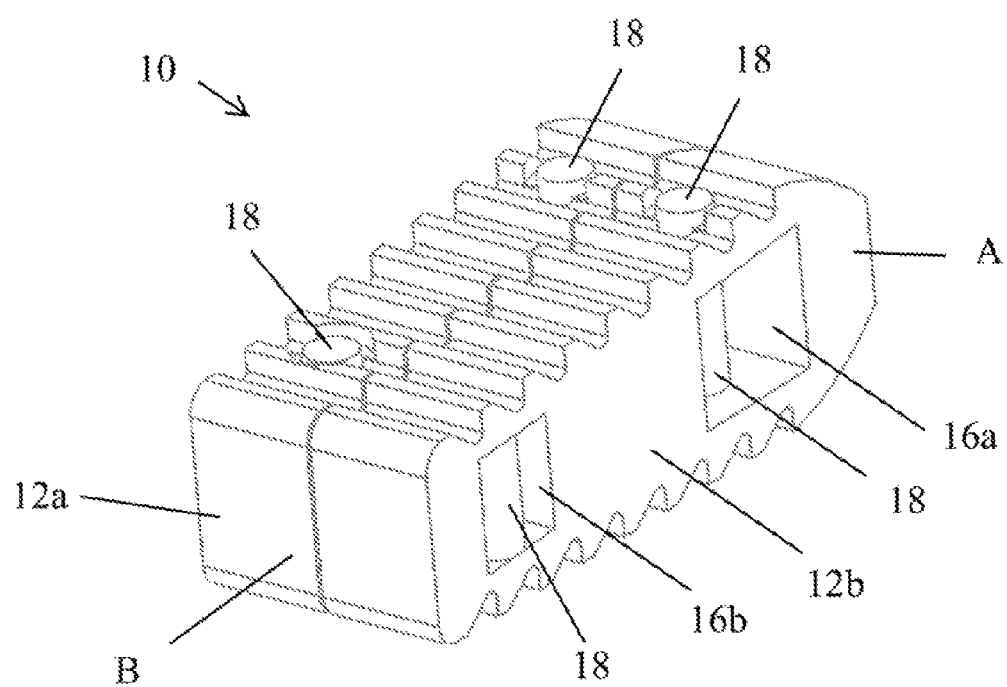
FIG. 2 is a three-quarters perspective view of an embodiment according to the present invention from the back.

With reference to FIGS. 1 and 2, an interbody fusion cage 10 according to the present invention includes a main body 11 consisting of two similarly-shaped support elements 12*a* and 12*b* each preferably having an elongate shape and a compact cross section to facilitate insertion of the cage 10 into the fully or partially evacuated interbody space of the patient through minimally invasive means. Prior to insertion of the cage 10 into the interbody space, support elements 12*a* and 12*b* are held in alignment by a peg-and-recess connection, as described below, such that the side of support element 12*a* is in contact with the side of support element 12*b*.

Support elements 12*a* and 12*b* have a front portion A which preferably has a smaller tapered cross section than the main portion of the support element 12 such that the front portion A forms the shape of a flattened point on the front of support element 12 to further facilitate insertion of the cage 10 into the interbody space through a narrow opening in the patient's body. Support elements 12*a* and 12*b* also have a back portion B at the opposite end of support elements 12*a* and 12*b* along the elongate axis of the support element 12.

Opposing top and bottom portions along the elongate axis of support elements 12*a* and 12*b* are preferably textured with, for example, multitude of ridges 14 for increased frictional engagement with the adjacent bone upon insertion of the cage 10 into the interbody space. Ridges 14 are preferably in the form of backwards-leaning teeth such that the cage 10 moves more easily in a frontal direction for insertion into the interbody space and less easily in a backwards direction to prevent the cage 10 from easily sliding out of the interbody space once inserted or during the insertion process. Ridges 14 may also take the form of grooves, knurling or other surface texture to increase friction with the adjacent bone after insertion of the cage 10 into the interbody space.

The length of the support elements 12, as measured from the front portion A to the back portion B of the support elements 12, is preferably from 35 mm to 60 mm and is selected by the surgeon depending on the physiology of the particular patient in which the cage 10 will be implanted. The height of the support elements 12 as measured between the opposing top and bottom portions containing ridges 14 is selected by the surgeon generally to replicate the natural height of the interbody space taking into account the thickness of the support elements 12 and anticipated subsidence during fusion. The height of the support elements 12 preferably decreases towards the front portion A of the support elements 12 as described above to facilitate insertion of the cage 10 into the interbody space whereby the cage 10 is inserted front first into the opening used to access the interbody space. The width of support elements 12 need only be large enough to accommodate pins 18 as described below. An exact width for support elements 12 may be dictated by physiology of the particular patient and/or the amount of weight that support elements 12 will be required to bear, etc.

In the depicted embodiment, support elements 12 further have openings 16*a* and 16*b* that extend from one side of the support element 12 through to the other side of support element 12, where the sides of support elements 12 in which the openings are formed are preferably perpendicular to both the top and bottom portions of support elements 12 and to the front A and back B portions of support elements 12. Openings 16a and 16b preferably have a uniform cross section, the height and width of which does not exceed the corresponding dimensions of the support elements 12 and the length of which corresponds to the width of the support elements 12. The openings 16 are also sized so as to accommodate two such openings 16 along the side of each of the support structures 12a and 12b. Opening 16a is preferably located as far towards the front portion A of the support structure 12 as possible and opening 16b is preferably located as far towards the back portion B of the support structure 12, consistent with the goal of maintaining the integrity of the structures 12a and 12b, to accommodate a maximum volume of graft material as set forth below.

Openings 16 are designed in accommodate access to the middle portion of pins 18, which extend perpendicular to the length of openings 16 from the top portion to the bottom portion of support bodies 12. As shown in FIGS. 1 and 2, pins 18 may either extend all the way through the top and bottom portions of support elements 12 or may not be long enough to breach the surface of top and bottom portions of support elements 12. In the event that the tops or bottoms of pins 18 are exposed through the top Or bottom of support elements 12, it is preferred that the pins 18 do not extend above the highest level of ridges 14 on either the top or bottom portions of support elements 12 in such a way as to prevent ridges 14 from making a full contact with the adjacent bone after insertion of the cage 10 into the interbody space.

Although not visible in FIGS. 1 and 2, pins 18 anchor ribbons 24 between support element 12a and support element 12b. In one preferred embodiment, the pins 18 contained within support element 12b are attached to one end of a ribbon 24, the width of which is preferably slightly less than the height of opening 16 so that ribbon 24 may pass through without wrinkling, cupping or otherwise deforming. In the preferred embodiment, the remainder of ribbon 24, less that portion of ribbon 24 that extends between pin 18 in support element 12b and pin 18 in support element 12a, is wrapped or spooled around pin 18 in support element 12a, Also in the preferred embodiment, pin 18 in support element 12b, to which ribbon 24 is attached, is fixed in place, while pin 18 in support element 12a, around which ribbon 24 is wrapped, is free to turn on its axis so as to allow ribbon 24 to unspool from its position around pin 18 in support element 12a. As will be seen with reference to FIGS. 3 through 8, the ribbon 24 and pin 18 construction is designed so that when support elements 12a and 12b are separated by the surgeon after insertion of the cage 10 into the patient, the ribbons 24 will deploy between structural elements 12a and 12b through the force of pin 18 in structural element 12b pulling on the fixed end of ribbon 24 and causing pin 18 in structural element 12a to turn so that the ribbon 24 will unravel and extend between structural elements 12 as they separate.

Figure 9:
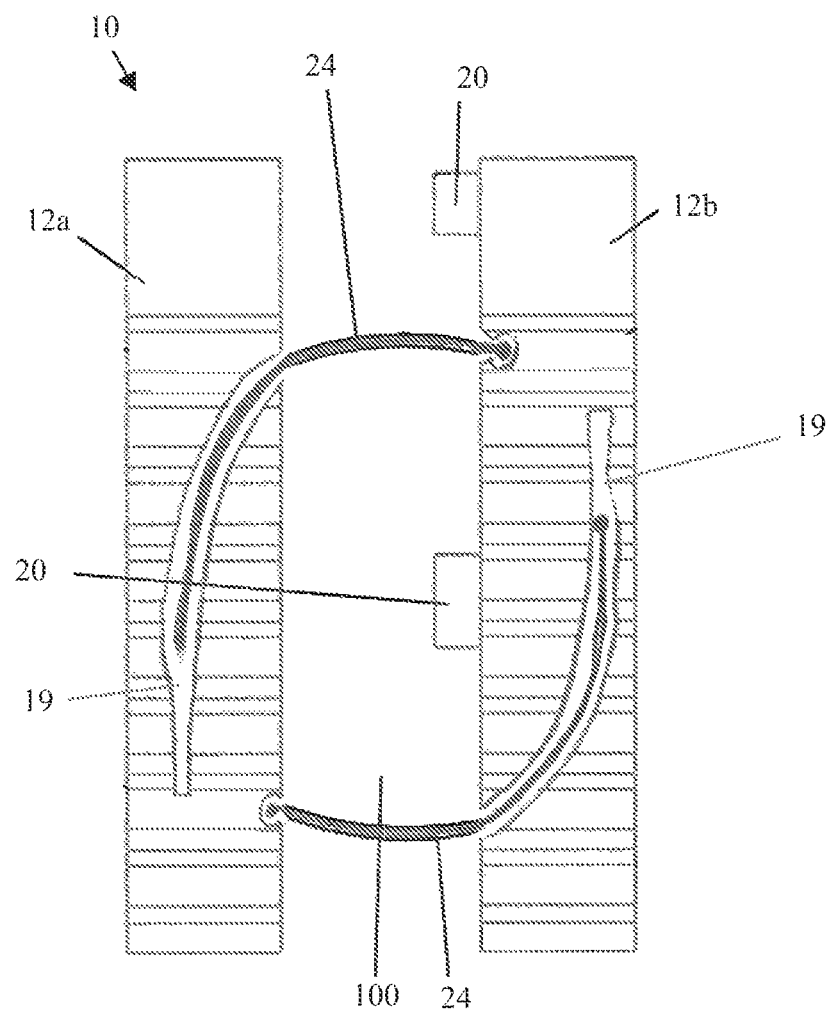
FIG. 9 is a perspective view of an alternate embodiment according to the present invention from above.

In alternate embodiment of the invention, depicted in FIG. 9, the ribbon 24 is affixed at one end to a pin 18 in one of the support elements 12 while the opposite end is received in a narrow channel or slot 19 cut longitudinally in the opposite support element 12 rather than being spooled on a pin. The channel turns or slightly curves to exit the inside surface of the support element and is cooperatively aligned where it exits the side inside surface with the pin 18 in the opposite support element. A slight necking of the channel width where it exits the inside surface of the support member serves to prevent the distal end of the ribbon 24 from fully exiting the channel through the side wall as the support elements 12 are separated, the distal end of the ribbon being provided with a slight enlargement that cannot pass through the narrowed channel exit.

In other preferred embodiments, only one ribbon 24 extends between adjacent pins 18 that are located in the front portions A of support elements 12a and 12b, while the pins 18 at the back portion B of support elements 12 accommodate a ribbon and suture mechanism as more fully described below. In yet another preferred embodiment, both sets of pins, i.e. the set at the front portion A of support elements 12 and the set at the back portion B of support elements 12, accommodate a ribbon and suture mechanism as more fully described below.

Figure 3:
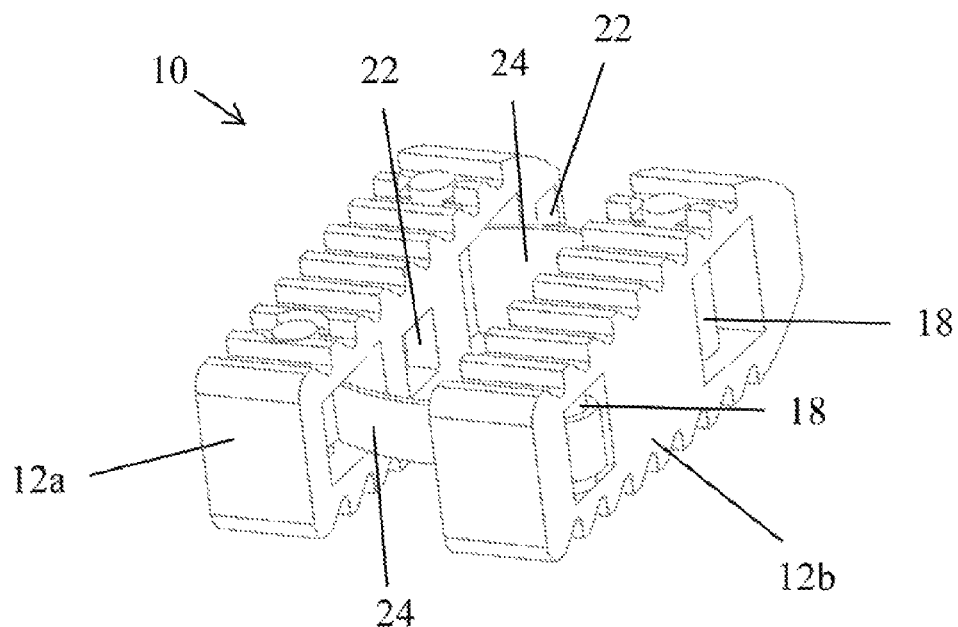
FIG. 3 is a three-quarters perspective view of an embodiment according to the present invention from the back.
Figure 4:
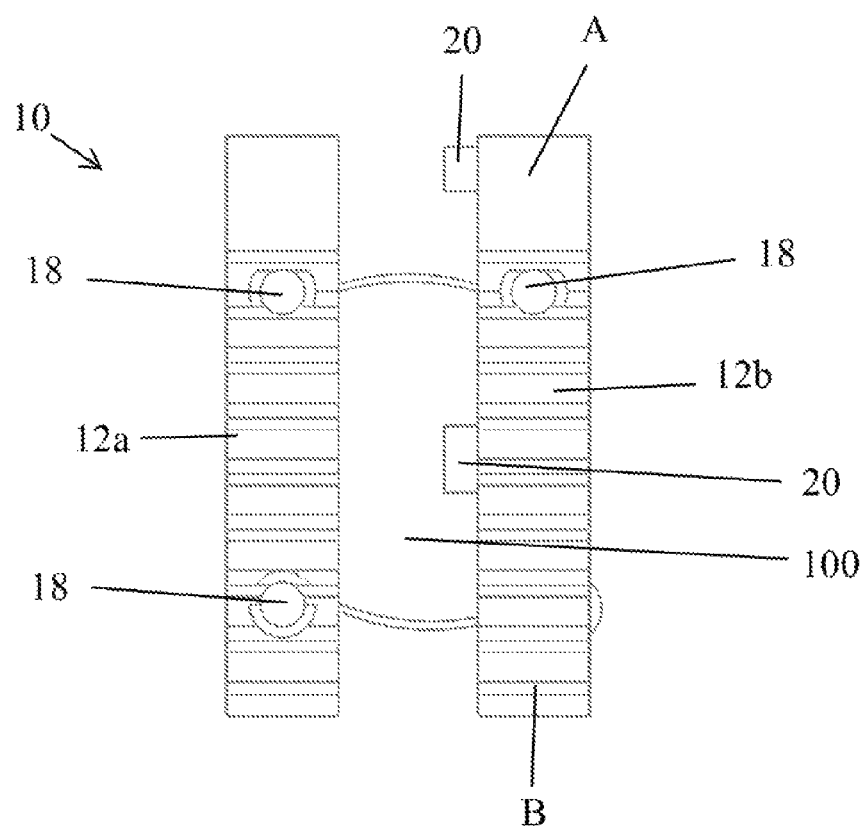
FIG. 4 is a perspective view of an embodiment according to the present invention from above.

In yet another preferred embodiment, one or both of ribbons 24 is couched between support elements 12 prior to their expansion, having one end fixedly attached to pin 18 in support element 12a and the other end fixedly attached to pin 18 in the corresponding opening 16 in support element 12b, rather than having one end spooled on a pin 18. In this preferred embodiment, the middle portion of ribbons 24 that are not fixedly attached to pins 18 may be folded once inwardly on itself along its longitudinal axis to allow it to lay flat against the inward facing sides of support elements 12a and 12b while cage 10 is closed. To accommodate this configuration of ribbons 24 while cage 10 is closed, the recess 22 and peg 20 formed between openings 16a and 16b, as depicted in FIG. 3, and as further described below, may be omitted. Thus, when cage 10 is opened by the surgeon after insertion into the patient, the movement of support elements 12a and 12b away from each other cause ribbons 24 to tighten up and move into position to contain graft material as shown in FIGS. 3 and 4. Preferably, the ribbons 24 according to this preferred embodiment are formed of elastically deformable material, as described in further detail below, such that the surgeon will be able to move or deform them to provide him access to pocket 100 after expansion of cage 10 to insert graft material therein. In accordance with the present embodiment, both ribbons 24 may be couched between support elements 12a and 12b prior to insertion of cage 10, or either one of the two ribbons 24 may be so couched while the other may be housed within support elements 12a and/or 12b as described above with reference to other preferred embodiments of the present invention.

Ribbon 24 are generally flat planar elements created from an elastically deformable material (i.e., spring-like) or, preferably, from a shape memory alloy such as Nitinol™. Ribbon 24 may alternately be formed of a biocompatible polymer thin films such as polyetheretherketone (PEEK), polyethylenes (such as BoPET), polypropylene, polyphenylene (SRP), polycarbonate, polyphenylsulfone (PPSU), polysulfone (PSU) and Polyoxymethylene (POM) as well as silicone rubber sheets.

With reference to FIGS. 3 and 4, the peg-and-recess connection that holds support elements 12a and 12b together prior to insertion into the interbody space is visible upon separation of the support elements 12. Peg 20 extends from an inward-facing side of support element 12b corresponding to the side that faces support element 12a. Recess 22 comprises an opening in the inward-facing side of support element 12a such that when support elements 12a and 12b are in contact, when the cage 10 is in a "closed" position, peg 20 fits snugly into groove 22 to align the support elements 12a and 12b. The peg and recess connection described herein should be secure enough to hold support elements 12a and 12b in position relative to each other prior to insertion, but should not be so snug as to prevent the easy separation of support elements 12a and 12h with an appropriate separation tool after insertion of the cage 10 into the interbody space as set forth below. In a preferred embodiment, support elements 12 are held together by the operation of two separate peg-and-recess connections along the length of their elongate axes. FIGS. 3 and 4 are referenced here to illustrate the means by which support elements 12a and 12b are held together in the starting or closed position of the cage 10, but it will be understood that peg 20 and groove 22 will not be visible to the eye prior to insertion of the cage 10 into the interbody space as set forth below.

With further reference to FIGS. 1 and 2, after full or partial evacuation of the interbody space by the surgeon through minimally invasive means, cage 10 is inserted front portion A first into the interbody space through the opening made by the surgeon for evacuation of the same. As described above, the cage 10 is sized and shaped so as to allow for easy insertion of the cage 10 into the interbody space through as small an opening as possible in the patient's body and to allow the cage 10 to "grip" the adjacent bone upon insertion through the operation of the ridges 14 that then come into contact with the bone. The cage 10 advantageously remains in the closed position, with support elements 12a and 12b in contact by operation of the peg-and-recess connection, throughout the entire process of insertion of the cage 10 into the interbody space and positioning of same by the surgeon.

With reference to FIGS. 3 and 4, once the cage 10 has been properly positioned in the interbody space, the surgeon may utilize a tool, which may advantageously be integrated into the insertion tool used to insert the cage 10 into the interbody space, to move the cage 10 into the "open" position by laterally separating the support elements 12a and 12b. Support elements 12 will advantageously be separated as far as possible while both remain in the interbody space to allow for maximum volume of graft material as described below. It be understood that the tool used to separate support structures 12 may be chosen by the surgeon to suit the conditions of the individual patient and operation and may be sized so as to be accommodated by the opening created during the minimally invasive procedure.

Upon opening of cage 10 after insertion, ribbons 24 are deployed from their starting state around pins 18 in support elements 12a to their open state as shown in FIGS. 3 and 4 through the movement of the support structures 12 apart from each other, which pulls ribbons 24 taught causing free pin 18 in structural element 12a to spin and release the required amount of slack to allow the ribbons 24 to extend between support structures 12a and 12b. Deployment of ribbons 24 forms a pocket 100 into which graft material may be inserted. Ribbons 24 are preferably supple enough to allow the surgeon to move them slightly up or down to provide him access to pocket 100 to insert the graft material. Ribbons 24 serve to hold graft material in place between support elements 12 during the 18-24 months generally required for the spinal fusion to take place. In this way, cage 10 provides a relatively large pocket 100 for insertion of a large volume of graft material with a relatively compact cage 10 that can be inserted through a relatively small hole in its closed state, thus allowing for a minimally invasive operation. Cage 10 also provides a method for ALIF or PLIF without the necessity to load graft material into the cage prior to insertion into the interbody space.

Figure 5:
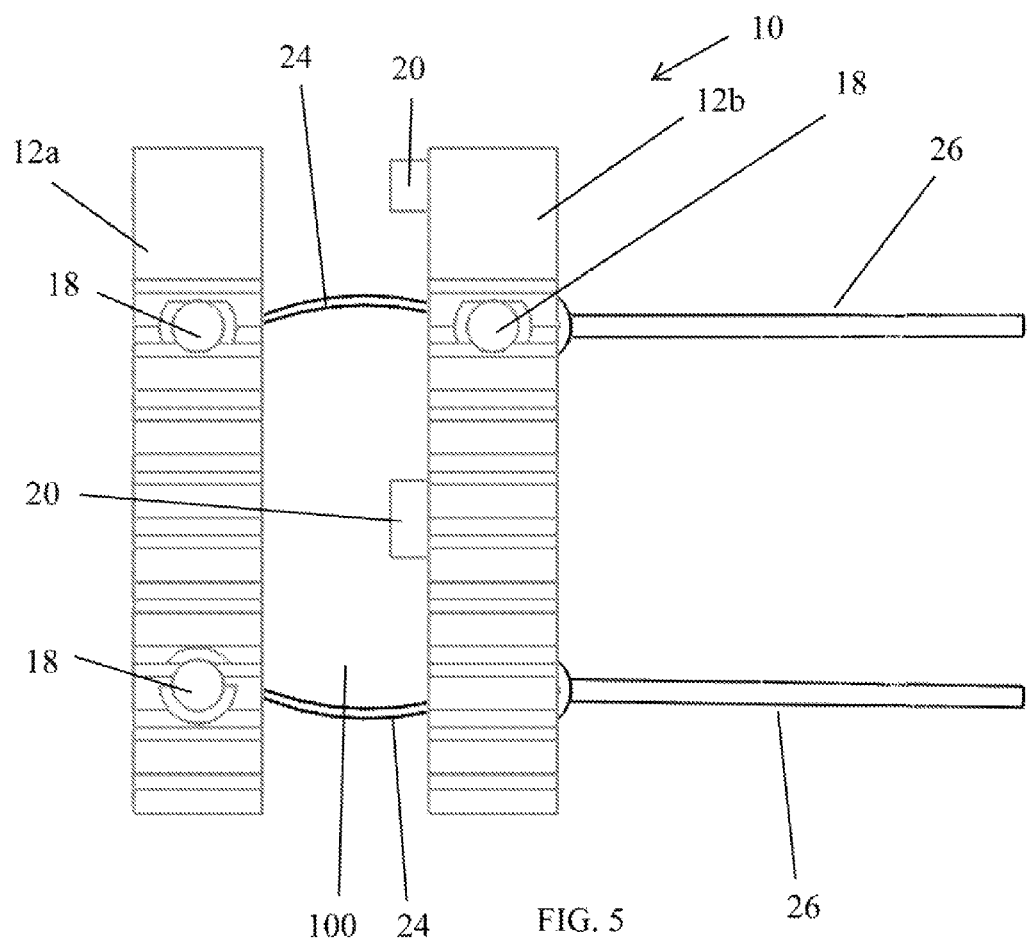
FIG. 5 is a perspective view of an alternate embodiment according to the present invention from above.
Figure 6:
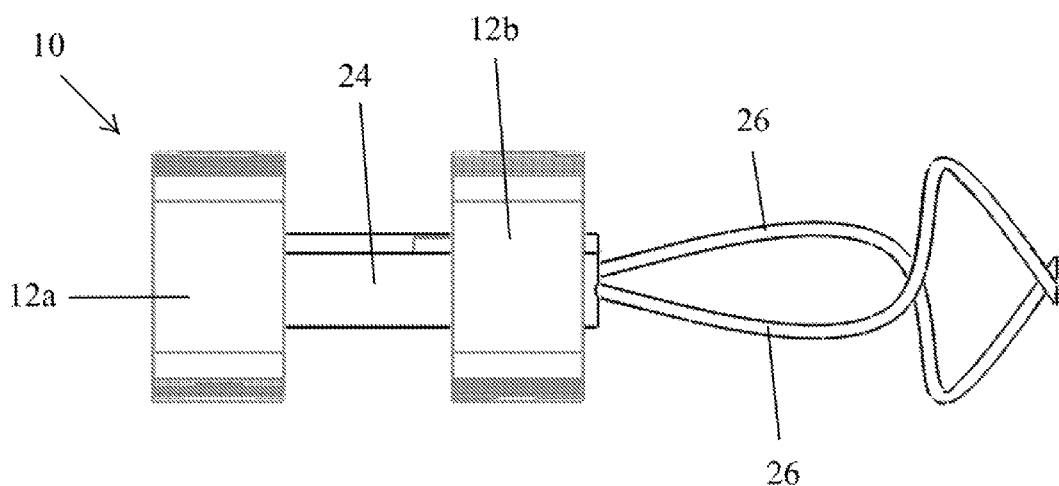
FIG. 6 is a perspective view of an alternate embodiment according to the present invention from the back.
Figure 7:
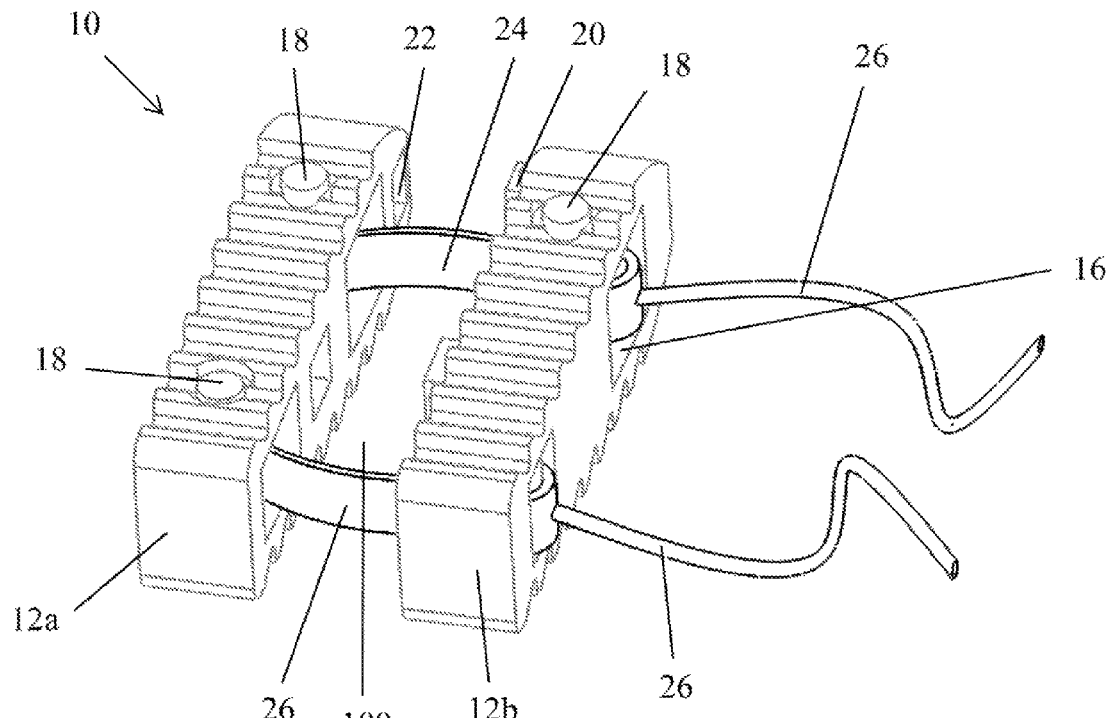
FIG. 7 is a three-quarters perspective view of an embodiment according to the present invention from the back.

With reference to FIGS. 5 through 7, another embodiment of the cage 10 is depicted, in the second preferred embodiment, one or both ribbons 24 are deployed through the operation of a suture 26 connected to one end of the ribbon(s) 24. In the second preferred embodiment, the remainder of ribbon 24 is stored in a position where it is wrapped around free pin 18 in support structure 12a. In embodiments using this ribbon and suture mechanism, when structural elements 12a and 12b are separated, it is the suture 26, and not the ribbon 24, which deploys to extend between structural element 12a and 12b. Suture 26 is preferably a monofilament element extending from the free end of the ribbon 24 and may be integrally formed therewith or affixed to by mechanical or other means. Suture 26 is preferably created from an elastically deformable material (i.e., spring-like) or, preferably, from a shape memory alloy such as Nitinol™, similar to the material used to form ribbons 24. However, suture 26 is narrower than ribbon 24, allowing the surgeon more access to pocket 100 for insertion of the graft material after expansion of the cage 10. Upon separation of the structural element 12a and 12b, the suture 26 extends through the opening 16 in the opposing structural element 12. After insertion of the graft material, the surgeon may pull the free end of suture 26 causing the ribbon 24 to unspool and deploy between support structures 12a and 12b as shown in FIG. 7. Upon passing through structural element 12b, suture 26 will be forced through a narrow opening (not shown in drawings) which will "pinch off" suture 26 and prevent it from retracting backwards into structural element 12b or into pocket 100. After ribbon 24 is entirely deployed between structural elements 12a and 12b, the surgeon may trim the excess of suture 26 and ribbon 24 that extend beyond the structural element 12b.

In addition to the advantages pointed out with respect to the first embodiment above, the second preferred embodiment advantageously provides the surgeon with easier access to the pocket 100 for insertion of the graft material after the cage 10 is opened. The surgeon may insert the graft material while only the thin suture 26 extends between structural elements 12a and 12b and in front of pocket 100, then after insertion of the graft material, may pull the suture so that the wider ribbon 24 more comprehensively covers the opening between structural elements 12a and 12b and forms a more secure pocket 100 which more effectively holds graft material in place during fusion.

Figure 8:
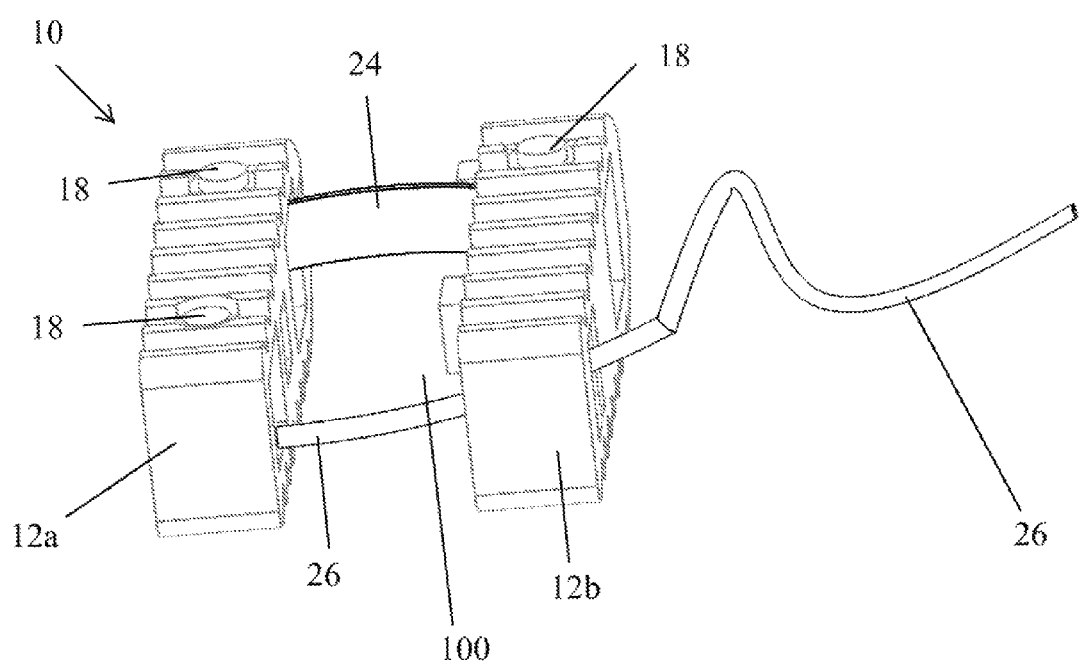
FIG. 8 is a three-quarters perspective view of yet another embodiment according to the present invention from the back.

With reference to FIG. 8, a third embodiment of cage 10 is depicted. The third embodiment utilizes both the mechanically deployed ribbon as described in reference to the first embodiment and FIGS. 1 through 4, as well as the ribbon and suture mechanism as described in the second embodiment of the cage 10. In this third embodiment, the mechanically deployed ribbon is deployed between pins 18 in the front potion A of structural elements 12, the front portion A being that which is inserted first into the interbody structure. In addition, the ribbon and suture mechanism described above operates between the pins 18 at the back portion B of structural elements 12, the back portion B being on the side of the pocket 100 to which the surgeon has access through the opening in the patient's body to insert the graft material. This configuration allows the surgeon easy access to the pocket 100 to insert the graft material around the suture 26, while deployed ribbon 24 prevents graft material from slipping out of the back of pocket 100 towards the front portion A of structural elements 12. After insertion of the graft material, the surgeon may then pull the suture 26 to expose ribbon 24 and create a secure pocket 100 to hold the inserted graft material in place during fusion.

The above-described embodiments provide a cage 10 that rigidly immobilizes the spine all directions, is strong enough to withstand repeated loadings, and has a modulus of elasticity similar to that of cortical bone. The cage 10 as set forth in the above-described embodiments is also be easy to insert by open or minimally invasive methods because of its relatively compact design upon insertion in the closed position. Cage 10 thus balances the competing priorities of being small enough to be inserted through the incisions of minimally invasive techniques while also being large enough to fill a significant portion of the interbody space and present a significant area to the vertebral surface in which graft material can be inserted and retained to promote growth.

It should be understood that the disclosure may be constructed of a variety of suitable surgical grade materials including stainless steel and titanium as well as composite materials having suitable strength and corrosion resistance properties should such materials be approved for surgical implantation. This application is therefore intended to cover any variations, uses, or adaptations of the invention using its general principles. Further, this application is intended to cover such departures from the present disclosure as come within known or customary practice in the art to which this invention pertains.

I claim:

1. An interbody fusion cage for insertion between adjacent vertebra, comprising:
    a body portion comprising a pair of support elements each having an upper surface and a lower surface joined by an inner surface and an outer surface, said pair of support elements movable from a first position in which the inner surface of the first of said pair of support elements is engaged to the inner surface of the second of said pair of support elements along a plane of engagement, and a second position in which said inner surfaces are disengaged each of said pair of support elements further comprising a pair of pins;
    a first ribbon having a first end wrapped about one of the pins of one of said support elements and engaged at a second end to one of the pins of the other support element, said first ribbon being received within said first or said second support elements when said support elements are in said first position;
    a second ribbon having a first end wrapped about one of the pins of one of said support elements and engaged at a second end to another of the pins of the other support element, said second ribbon being received within said first or said second support elements when said support elements are in said first position;
    whereby said first ribbon and said second ribbon are drawn from said first or second support elements when said support elements are moved to said second position thereby permitting movement in a direction perpendicular to the plane of engagement of said first and second support elements while resisting movement in a direction along said plane of engagement, and thereby defining an area bordered by said support elements and said ribbons in which to contain graft material.

2. The interbody fusion cage of claim 1 wherein said first support element further comprises a plurality of recesses in said inner surface of said first support element;
    wherein said second support element comprises a plurality of protrusions extending from said inner surface of said second support element, said protrusions cooperatively sized, shaped and positioned to be received in said recesses; and
    wherein said first support element is engaged to said second support element in said first position by receipt of said protrusions in said recesses.

3. The interbody fusion cage of claim 1 wherein said first support element further comprises a first pin and a second pin and wherein said second support element further comprises a third pin and a fourth pin; and
    wherein said first ribbon is wrapped at said first end about said first pin and is affixed at said second end to said second pin.

4. The interbody fusion cage of claim 3 wherein said first ribbon is spooled around said first pin when said first support element is engaged to said second support element.

5. The interbody fusion cage of claim 4 wherein said second ribbon is spooled around said third pin when said first support element is engaged to said second support element.

6. The interbody fusion cage of claim 1 wherein said second ribbon further comprises a suture affixed to said second end of said second ribbon, said suture passing through a hole in said second support element whereby said second ribbon can be drawn from said first support element and engaged to said second support element when said first and second support element are in said second position.

7. The interbody fusion cage of claim 6 wherein said suture is a monofilament.

8. The interbody fusion cage of claim 1 wherein said body portion further comprises a first channel in said first support element, said first channel extending to a first opening in said inner surface of said first support element, and a second channel in said second support element, said second channel extending to a second opening in said inner surface of said second support element;
    wherein said first ribbon is received within said first channel and said second ribbon is received within said second channel when said support elements are in said first position.

9. The interbody fusion cage of claim 8 wherein said second support member further comprises a first pin cooperatively aligned with said first opening when said support elements are in said first position, said first ribbon extending through said first opening and engaged to said first pin, and said first support member further comprises a second pin cooperatively aligned with said second opening when said support elements are in said first position, said second ribbon extending through said second opening and engaged to said second pin.

10. The interbody fusion cage of claim 8 wherein said second ribbon further comprises a suture affixed to said second end of said second ribbon, said suture passing through a hole in said first support element whereby said second ribbon can be drawn from said second channel through said second opening and engaged to said first support element when said first and second support elements are in said second position.

11. The interbody fusion cage of claim 1 wherein upper surfaces and said lower surfaces of said pair of support elements are each defined by a plurality of ridges.

12. The interbody fusion cage of claim 1 wherein said ribbons are flat planar elements created from an elastically deformable material.

13. The interbody fusion cage of claim 1 wherein said ribbons are flat planar elements created from a shape memory alloy.

14. An interbody fusion cage for insertion between adjacent vertebra, comprising:
    a body portion comprising a pair of support elements each having an upper surface and a lower surface joined by an inner surface and an outer surface, said pair of support elements movable from a first position in which the inner surface of the first of said pair of support elements is engaged to the inner surface of the second of said pair of support elements along a plane of engagement, and a second position in which said inner surfaces are disengaged, each of said pair of support elements further comprising a pair of pins;
    a first ribbon having a first end to said wrapped about one of the pins of one of said support elements and engaged at a second end to one of the pins of the other support element, said first ribbon being received within said first or said second support elements when said support elements are in said first position;

a second ribbon having a first end wrapped about one of the pins of one of said support elements and engaged at a second end to another of the pins of the other support element, said second ribbon being received within first or said second support elements when said support elements are in said first position;

whereby said first ribbon and said second ribbon extend from said first and second support elements when said support elements are in said second position thereby permitting movement in a direction perpendicular to the plane of engagement of said first and second support elements while resisting movement in a direction along said plane of engagement, and thereby defining an area bordered by said support elements and said ribbons in which to contain graft material.

15. The interbody fusion cage of claim 14 wherein said first support element further comprises a plurality of recesses in said inner surface of said first support element;

wherein said second support element comprises a plurality of protrusions extending from said inner surface of said second support element, said protrusions cooperatively sized, shaped and positioned to be received in said recesses; and wherein said first support element is engaged to said second support element in said first position by receipt of said protrusions in said recesses.

16. The interbody fusion cage of claim 14 wherein said first support element further comprises a first pin and a second pin and wherein said second support element further comprises a third pin and a fourth pin; and wherein said first ribbon is wrapped at said first end about said first pin and is affixed at said second end to said second pin.

17. The interbody fusion cage of claim 14 wherein upper surfaces and said lower surfaces of said pair of support elements are each defined by a plurality of ridges.

18. The interbody fusion cage of claim 14 wherein said ribbons are flat planar elements created from an elastically deformable material.

19. The interbody fusion cage of claim 14 wherein said ribbons are flat planar elements created from a shape memory alloy.

* * * * *